(12) United States Patent
Stamm et al.

(10) Patent No.: US 6,353,127 B1
(45) Date of Patent: Mar. 5, 2002

(54) α-CHLORONITRILES PRODUCTION METHOD

(75) Inventors: Armin Stamm, Mainz; Jakob Fischer, Kirchdorf; Jochem Henkelmann, Mannheim; Wolfgang Siegel, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,349

(22) PCT Filed: Oct. 29, 1999

(86) PCT No.: PCT/EP99/08213

§ 371 Date: Apr. 25, 2001

§ 102(e) Date: Apr. 25, 2001

(87) PCT Pub. No.: WO00/26183

PCT Pub. Date: May 11, 2000

(30) Foreign Application Priority Data

Nov. 4, 1998 (DE) .......................................... 198 50 856

(51) Int. Cl.$^7$ .............................................. C07C 255/00
(52) U.S. Cl. ...................................................... 558/460
(58) Field of Search ......................................... 558/460

(56) References Cited

U.S. PATENT DOCUMENTS 4,476,059 A    10/1984    Davidson

FOREIGN PATENT DOCUMENTS

EP    518 412    12/1992

OTHER PUBLICATIONS

J4 9001–516 Abstract (1974).
J.Chem.Soc. PartIII, 1054–1061, Ritchie (1935).

*Primary Examiner*—Joseph K. McKane
*Assistant Examiner*—Joseph Murray
(74) *Attorney, Agent, or Firm*—Keil & Weinkauf

(57) ABSTRACT

The invention relates to a process for the preparation of α-chloronitriles by reaction of cyanohydrins of aldehydes or ketones with phosgene using a phosphine oxide as catalyst.

7 Claims, No Drawings

α-CHLORONITRILES PRODUCTION METHOD

The invention relates to a process for the preparation of α-chloronitriles by reaction of cyanohydrins with phosgene.

α-Chloronitriles of the formula I can be used as versatile intermediates in a number of reactions. Thus, for example, it is possible to obtain β-chloroamines by hydrogenation of the nitrile group. Acidic hydrolysis of the nitrile group gives α-chlorocarboxylic acids, which are only obtainable by another method by chlorination of carboxylic acids. By exchanging the chlorine substituents it is possible to prepare a number of other secondary products.

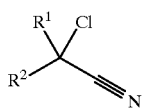
(I)

The literature discloses a number of synthesis routes for the preparation of α-chloronitriles. A frequently used process is the chlorination of nitriles in the α-position. A variety of chlorine carriers are suitable for this purpose. For example, chlorination reactions which chlorine, sulfonyl chloride, alkali metal and alkaline earth metal hypochlorites and with alkali metal salts of N-chloroarylsulfonamides have been described.

However, these chlorination reactions have the disadvantage that α,α-dichloronitriles are formed in relatively large amounts as secondary products or even as the main product.

In another synthesis route for the preparation of α-chloronitriles, cyanohydrins of the formula II are reacted with chlorine with substitution of their hydroxyl group.

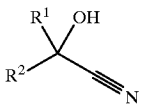
(II)

Cyanohydrins can be readily synthesized by addition of hydrocyanic acid to aldehydes and ketones. Substitution of the hydroxyl group for a chlorine substituent can be carried out with a variety of inorganic reagents. The literature frequently describes the use of inorganic acid halides. Suitable compounds are, for example, phosphorus pentachloride, phosphorus trichloride and thionyl chloride.

Phosgene is particularly suitable since in a reaction of phosgene with cyanohydrins only carbon dioxide forms as secondary product, which escapes from the system in gaseous form. Furthermore, phosgene is a valuable chlorinating reagent, meaning that the reaction with phosgene is an economical route for the preparation of α-chloronitriles. Since phosgene on its own is too unreactive for the reaction with cyanohydrins at suitable reaction temperatures and pressures, the reaction is usually carried out in the presence of a catalyst.

J4 9001 516 (DW 0740037211V) describes a process for the preparation of chloroacetonitrile by reaction of glycolonitrile with phosgene using dimethylformamide (DMF) as catalyst.

J. Chem. Soc. 1935, p. 1059 discloses the reaction of acetaldehyde cyanohydrin with phosgene in the presence of equimolar amounts of pyridine. In the reaction, as well as the carbonate which forms as the main product, the corresponding α-chloronitrile is formed in 6% yield. As well as the small amounts of α-chloronitrile, a disadvantage of this process is that because pyridine is used as auxiliary base, the hydrochloride of the base is produced as coupling product, which on a larger scale hinders work-up and disposal.

It is an object of the present invention to provide a process for the preparation of α-chloronitriles which can be used for a large number of compounds by reaction of cyanohydrins of aldehydes and ketones with phosgene.

We have found that this object is achieved by a process for the preparation of α-chloronitriles by reaction of cyanohydrins of aldehydes or ketones with phosgene using a catalyst, where the catalyst is a phosphine oxide.

The process has the advantage that it can be used for a large number of compounds. Low-cost phosgene can be used, meaning that the process according to the invention is an economical route for the preparation of α-chloronitriles.

Furthermore, the only byproducts which forms is gaseous carbon dioxide, meaning that work-up of the reaction mixture is problem-free, or that the reaction discharge can be used directly, without work-up, for subsequent syntheses.

The process according to the invention produces α-chloronitriles of the formula I. The radicals $R^1$ and $R^2$ can be arbitrary, provided they are inert toward phosgene. They correspond to the radicals $R^1$ and $R^2$ of the cyanohydrins used in the process according to the invention, which are discussed later and to which reference is made here.

Catalysts which can be used are phosphine oxides, e.g. Trialkyl- and triarylphosphite oxides. They can be used as individual compounds or as mixtures of different phosphine oxides. Particularly suitable tri aryl-phosphine oxides are triphenylphosphine oxide and tri-p-halogenophenylphosphine oxides. Preferred trialkylphosphine oxides are those with C3- to C18-alkyl radicals, where the alkyl radicals can be identical or different, such as trihexyl-, tributyl-, trioctyl- and tri(2-ethylhexyl)phosphine oxide.

It is possible to use either solid or liquid phosphine oxides. Because they are easier to meter, liquid phosphine oxides are preferred. Very particular preference is therefore given to a liquid mixture of $C_6$- to $C_8$-trialkylphosphine oxides as catalyst, as sold, for example, under the trade name Cyanex® 923 by Cytec Industries Inc., N.J., USA.

The catalysts are generally used in an amount of from 0.5 to 5 mol %, preferably from 1 to 2.5 mol %, based on the cyanohydrin used.

Suitable cyanohydrins in the process according to the invention are cyanohydrins of the formula II. It is possible to use cyanohydrins of aldehydes or ketones, and the cyanohydrin of formaldehyde.

The radicals $R^1$ and $R^2$ can be arbitrary, provided they are inert toward phosgene.

Radicals containing NH, OH and SH groups are therefore excluded. $R^1$ and $R^2$ are generally independently of one another hydrogen, aliphatic, cycloaliphatic, aromatic or araliphatic radicals. These can be substituted with heteroatoms, or their carbon chains can be interrupted by heteroatoms. The aliphatic radicals can be branched or unbranched, as desired. They preferably contain from 1 to 12 carbon atoms. Examples of aliphatic radicals are methyl, ethyl, n-propyl, etc. Suitable cycloaliphatic radicals are preferably those having from 5 to 8 carbon atoms such as cyclopentyl or cyclohexyl. The aromatic radicals preferably have from 6 to 12 carbon atoms. The aromatic radicals can be unsubstituted or substituted by alkyl or aryl substituents or heteroatoms, as desired. The aromatic radicals are preferably mono- or disubstituted. Examples of aromatic radicals are phenyl and chlorophenyl. Suitable araliphatic radicals are preferably those having from 7 to 13 carbon atoms. An example of a preferred araliphatic radical is benzyl.

The cyanohydrins used are preferably the cyanohydrins of aldehydes (either $R^1$ or $R^2$ in formula II is H). Particular preference is given to the cyanohydrins of unbranched or branched aliphatic aldehydes, cyano-hydrins of unsubstituted aromatic aldehydes, in particular benzaldehyde cyanohydrin, or cyanohydrins of mono- or disubstituted aromatic aldehydes such as benzaldehyde or p-chlorobenzaldehyde.

The cyanohydrins used are obtainable by reaction of the corresponding aldehydes and ketones with hydrocyanic acid (hydrogen cyanide), as described, for example, by C. Grundmann in Houben-Weyl, 4th Edition, enlarged volume V, Part II, Chapter 2.1.3, page 413 to 414. According to this, the desired cyanohydrins are prepared by reaction of carbonyl compounds with hydrocyanic acid (=hydrogen cyanide). This equilibrium reaction is catalyzed, for example, by ion exchanger resins.

In a preferred embodiment, the reaction mixture comprising cyanohydrin obtained by the reaction of aldehydes or ketones with hydrocyanic acid is reacted directly, without prior isolation, with phosgene. It is therefore possible to dispense with work-up steps, thus making the process more economical.

The reaction according to the invention of the cyanohydrins with phosgene is generally carried out in an organic solvent inert toward phosgene. Preferred solvents are hydrocarbons. Particular preference is given to mono- or polysubstituted aromatic hydro-carbons, very particular preference to toluene, o-, m- or p-xylene or chlorobenzene.

In a further preferred embodiment, the solvent used in the initial charge is the α-chloronitrile desired as target product. In this variant it is possible to dispense with additional further solvent, and subsequent removal of the solvent is not required.

The process according to the invention is generally carried out at temperatures of from 50 to 150° C., preferably from 80 to 120° C., and at a pressure of from 0.8 to 1.2 bar, preferably at atmospheric pressure.

The phosgene can be used in the process according to the invention in gaseous form or in condensed form. It is preferable to introduce the phosgene into the reaction mixture in gaseous form.

In principle, the process can be carried out either continuously or discontinuously, preference being given to continuous operation. Very particular preference is given to continuous operation in which the target product (desired α-chloronitrile) is introduced initially.

The process can be carried out in any apparatus suitable for the reaction. For example, use is made of a phosgenation apparatus which includes an attached carbonic acid condenser.

In a preferred embodiment of the process, the solvent is initially introduced together with the catalyst and heated to the desired reaction temperature of generally from 50 to 150° C., preferably from 80 to 120° C. Phosgene is introduced into this initial charge until saturation. The running-in of the corresponding cyanohydrin is then started. Phosgene and cyanohydrin are then run in at the same time. After a post-reaction, excess phosgene is generally stripped out at temperatures of from 30 to 80° C., preferably 50° C. Nitrogen is generally used for the stripping.

Phosgene is generally used in a slight molar excess, based on the cyanohydrin used. The molar ratio between phosgene and cyanohydrin is preferably from 1 to 2:1. Particular preference is given to using phosgene in an excess of from 5 to 15 mol %, based on the cyanohydrin.

The reaction discharge is worked up using methods known to the person skilled in the art. Preferably, the mixture is fractionally distilled on a Vigreux column. In this case, the desired α-chloronitrile can be obtained in yields of generally from 50 to 90%, based on the cyanohydrin used.

The present invention further relates to the use of phosphine oxides as catalyst in the reaction of cyanohydrins of aldehydes or ketones with phosgene.

The examples below further illustrate the invention.

EXAMPLES

Example 1

α-Chlorovaleronitrile 150 g of toluene and 10.4 g (0.03 mol) of Cyanex® 923 are introduced into a phosgenation apparatus with attached carbonic acid condenser and heated. At 99° C., 17 g of phosgene are gassed in over the course of 10 minutes. Thereafter, over the course of 90 minutes, 140 g (1.5 mol) of 2-hydroxyvaleronitrile and a further 168 g (total =185 g or 1.87 mol) of phosgene are added in parallel. The temperature is maintained between 99 and 103° C. throughout. After a post-reaction of 80 minutes at 94° C., excess phosgene is stripped out using $N_2$ at 50° C. for 4.5 h. The discharge of 307 g is fractionally distilled on a 30 cm Vigreux column. The main fraction passes over at 9 mbar and a head temperature of 42° C. 150.6 g (85.3% of theory) of α-chlorovaleronitrile are isolated.

Example 2

Comparative Example to J4 9001 516

100 g of ortho-xylene and 3.1 g (0.02 mol) of diisobutylformamide are initially introduced at 48° C. Over the course of 10 minutes, 20 g of phosgene (0.2 mol) are gassed into the solution, the internal temperature increasing as a result to 59° C. Over the course of 5 h, 99 g (1 mol) of 2-hydroxyvaleronitrile and 84 g of phosgene are introduced in parallel at from 56 to 59° C. over the course of 5 h. After a post-reaction of 1.5 h at 58° C., excess phosgene is removed by stripping with $N_2$. The discharge comprises a mixture of chloroformate, carbonate and only from about 15 to 20% of α-chlorovaleronitrile.

Example 3

α-Chlorophenylacetonitrile 150 g of toluene and 7 g (0.02 mol) of Cyanex® 923 are initially introduced into a phosgenation apparatus with attached carbonic acid condenser and heated. At 99° C., 13 g of phosgene are gassed in over the course of 10 minutes. Thereafter, over the course of 2 hours, 192 g (1.44 mol) of benzaldehyde cyanohydrin and a further 149 g (total=172 g or 1.74 mol) of phosgene are added in parallel. The internal temperature is maintained between 99 and 102° C. throughout. After a post-reaction of 60 minutes at 99° C., excess phosgene is stripped out using $N_2$ at 50° C. for 2.5 h. The discharge of 359 g is fractionally distilled on a 30 cm Vigreux column. The main fraction passes over at 0.6 mbar and a head temperature of from 68 to 73° C. 192.7 g (88.3% of theory) of α-chlorophenylacetonitrile are isolated.

| Elemental analysis | calc.: | C: 63.4% | H: 4.0% | N: 9.2% |
|---|---|---|---|---|
| | | Cl: 23.4% | | |
| | found: | C: 63.3% | H: 4.0% | N: 9.3% |
| | | Cl: 23.6% | | |

Example 4

Chloroisobutyronitrile 150 g of o-xylene and 10.4 g (0.03 mol) of Cyanex® 923 are initially introduced into a phosgenation apparatus with attached carbonic acid condenser and heated. At from 97 to 103° C., 20 g of phosgene are gassed in over the course of 10 minutes. Thereafter, over the course of 5 hours, 67 g (0.8 mol) of acetone cyanohydrin and a further 72 g (total=92 g or 0.93 mol) of phosgene are added in parallel. The internal temperature is maintained at between 95 and 103° C. throughout. After a post-reaction of 30 minutes at 107° C., excess phosgene is stripped out using $N_2$ at 50° C. for 2 h. The discharge of 209.5 g comprises 42% of methacrylonitrile (by elimination of HCl) and 51 % of chloroisobutyronitrile and is fractionally distilled on a 30 cm Vigreux column. Since the HCl is eliminated thermally during the distillation, isolation is unsuccessful.

Example 5
α-Chlorobutyronitrile from propionaldehyde cyanohydrin 103.5 g of 2-chlorobutyronitrile (1 mol), prepared and distilled as in Example 1, and 7 g of Cyanex 923 (0.02 mol) are initially introduced and heated to 100° C. At from 100 to 116° C., over the course of 10 minutes, initially 18 g (0.18 mol) of phosgene are gassed in until reflux is reached. At from 100 to 116° C., over the course of 2 hours, a mixture of 138 g of propionaldehyde cyanohydrin (1.5 mol) and 10.5 g of Cyanex 923 (0.03 mol), and 214 g (2.15 mol) of phosgene are then metered in in parallel. After a post-reaction of 75 minutes at 100° C., excess phosgene is removed by stripping with nitrogen at 50° C. (1 hour). The crude discharge (267.3 g) comprises >95 GC area % of 2-chlorobutyronitrile. Distillation at 100 mbar and a head temperature of from 72 to 74° C. on a 30 cm column produces 228.8 g of 2-chlorobutyronitrile having a purity of 99.5%, corresponding to a distilled yield of 81%.

We claim:

1. A process for the preparation of α-chloronitriles by reaction of cyanohydrins of aldehydes or ketones with phosgene using a catalyst, wherein the catalyst is a phosphine oxide.

2. A process as claimed in claim 1, wherein the catalyst used is a mixture of $C_6$–$C_8$-tri-alkylphosphine oxides.

3. A process as claimed in claim 1, wherein the catalyst is used in an amount of from 0.5 to 5 mol %, based on the cyanohydrin used.

4. A process as claimed in claim 1, wherein the cyanohydrins used are prepared by reaction of aldehydes or ketones with hydrogen cyanide, and the resulting reaction mixture is reacted directly with phosgene without prior isolation.

5. A process as claimed in claim 1, wherein the reaction is carried out in an inert organic solvent.

6. A process as claimed in claim 5, wherein the α-chloronitrile to be produced is used as solvent.

7. A process as claimed in claim 1, wherein the reaction is carried out at temperatures of from 50 to 150° C.

* * * * *